United States Patent [19]
Livingstone et al.

[11] Patent Number: 5,474,081
[45] Date of Patent: Dec. 12, 1995

[54] METHOD AND APPARATUS FOR DETERMINING MAGNOCELLULAR PATHWAY DEFECT AND DYSLEXIA

[75] Inventors: Margaret S. Livingstone, Chestnut Hill; Albert M. Galaburda, Andover, both of Mass.

[73] Assignee: President and Fellows of Harvard College, Cambridge, Mass.

[21] Appl. No.: 154,634

[22] Filed: Nov. 18, 1993

Related U.S. Application Data

[63] Continuation of Ser. No. 938,947, Sep. 1, 1992, abandoned.
[51] Int. Cl.$^6$ .................................................. A61B 13/00
[52] U.S. Cl. .................................... 128/731; 128/745
[58] Field of Search .................................. 128/745, 731, 128/732; 351/205, 211, 222, 232, 246; 364/413.01, 413.02

[56] References Cited

U.S. PATENT DOCUMENTS

| | | | |
|---|---|---|---|
| 4,421,122 | 12/1983 | Duffy | 128/731 |
| 4,493,539 | 1/1985 | Cannon, Jr. | 351/205 |
| 4,528,989 | 7/1985 | Weinblatt | 128/745 |
| 4,676,611 | 6/1987 | Nelson et al. | 351/205 |
| 4,697,598 | 10/1987 | Bernard et al. | 128/731 |
| 4,753,246 | 6/1988 | Freeman | 128/731 |
| 4,832,480 | 5/1989 | Kornacker et al. | 351/246 |
| 4,869,264 | 9/1989 | Silberstein | 128/731 |
| 4,913,160 | 4/1990 | John | 128/731 |
| 4,926,969 | 5/1990 | Wright et al. | 128/731 |
| 4,953,968 | 9/1990 | Sherwin et al. | 351/211 |
| 5,065,767 | 11/1991 | Maddess | 128/745 |
| 5,083,571 | 1/1992 | Prichep | 128/731 |

FOREIGN PATENT DOCUMENTS

| | | |
|---|---|---|
| 0199218 | 10/1986 | European Pat. Off. . |
| 0256738 | 2/1988 | European Pat. Off. . |

OTHER PUBLICATIONS

Livingstone et al., "Physiological and Anatomical Evidence for Magnocellular Defect in Developmental Dyslexia", *Proc. Acad. Natl. Sci.* USA, vol. 88, pp. 7943–7947, Sep. 1991.

May et al, "Factor Scores Derived from Visual Evoked Potential Latencies Differentiate Good and Poor Readers", *Clin. Vision Sci.* vol. 7 No. 1, pp. 67–70, 1992 (month unknown).

S. Lehmkuhle et al., "The Effects of Uniform Field Flicker on Visual Evoked Potentials in Children with Reading Disability", *Investigative Opthomology and Visual Science*, Supplement, vol. 33 (1992) Abstract only. (month unknown).

*Primary Examiner*—Stephen C. Pellegrino
*Assistant Examiner*—Guy V. Tucker
*Attorney, Agent, or Firm*—Hamilton, Brook, Smith & Reynolds

[57] ABSTRACT

A method and apparatus determine defective magnocellular pathway in the visual system of a subject. Such determination of defective magnocellular pathway in turn is deterministic of dyslexia. The invention method and apparatus presents to a subject eye a series of patterns spatially varying in light intensity, such as a checkerboard pattern. Each pattern provides a certain respective degree of contrast between areas of varying light intensity. In displaying each checkerboard pattern, it is alternated with display of its contrast reverse pattern at a frequency between about 0.5 Hz and about 15 Hz. The temporal frequency from one checkerboard pattern to the next checkerboard pattern in the displayed series of patterns is in the range of about 30 patterns per minute to hundreds of patterns per minute. Response of the eye, such as the visually evoked potential, to each pattern is measured as the pattern is being displayed. And the measured responses are compared to a predetermined range of standard/normal responses for the given displayed patterns. Measured responses falling outside of the predetermined range of standard/normal responses indicate a magnocellular pathway defect, and hence dyslexia.

26 Claims, 3 Drawing Sheets

METHOD AND APPARATUS FOR DETERMINING MAGNOCELLULAR PATHWAY DEFECT AND DYSLEXIA

This is a continuation of application Ser. No. 07/938,947, filed on Sep. 1, 1992, now abandoned.

BACKGROUND OF THE INVENTION

In general, the human visual system is formed of two major processing pathways referred to as the magnocellular pathway and the parvocellular pathway. These two subdivisions or pathways remain largely segregated and independent throughout the visual system. The two pathways begin in the retina but are most apparent in the lateral geniculate nucleus (LGN). In the LGN, cells in the ventral or magnocellular layers are larger than cells in the dorsal or parvocellular layers. In the retina and LGN, the magno and parvo subdivisions differ physiologically in four major ways: color selectivity, contrast sensitivity, temporal resolution, and acuity.

In particular, fast, low contrast visual information is carried by the magnocellular subdivision or pathway, and slow high contrast information is carried by the parvocellular subdivision/pathway. This functional segregation, begun in the retina, continues throughout the visual system, possibly even up through higher cortical association areas. Therefore, a problem specific to the magnocellular pathway could originate at any level from the retina to prestriate visual cortical areas, and it would be difficult, using behavioral tests, to localize such perceptual defects.

For example, development dyslexia is the selective impairment of reading skills despite normal intelligence, sensory acuity, motivation and instruction. Several perceptual studies have suggested that dyslexic subjects process visual information more slowly than normal subjects. The flicker fusion rate, which is the fastest rate at which a contrast reversal of a stimulus can be seen, is abnormally slow in dyslexic children at low spatial frequencies and low contrast. When two visual stimuli are presented in rapid succession, the two images fuse and appear as a single presentation. The temporal separation necessary to distinguish two presentations measures visual persistence, and for dyslexic children the temporal separation is a hundred milliseconds longer than for normal children, particularly for low spatial frequency stimuli. Dyslexic subjects also have trouble distinguishing the order of two rapidly flashed visual stimuli. In contrast, dyslexics perform normally on test having prolonged stimulus presentations.

Thus, past perceptual studies suggest that the fast functioning part of the visual system is slowed down in dyslexia. Tests using behavioral methods have been unable to more specifically detect or localize the perceptual defects involved in dyslexia. On the other hand, further studies have been made to more accurately determine dyslexia using visually evoked potentials in response to stimuli at low spatial frequency (see "Factor Scores Derived From Visual Evoked Potential Latencies Differentiate Good and Poor Readers", by James G. May et al., *Clin. Vision Sci.*, Vol. 7, No. 1, pages 67–70, 1992) and visually evoked potentials in response to background flicker (see "The Effects of Uniform Field Flicker on Visual Evoked Potentials in Children With Reading Disability" by Steven Lehmkuhle et al., *Investigative Opthomology and Visual Science*, Supplement, Vol. 33 (1992), page 718.

SUMMARY OF THE INVENTION

The foregoing perceptual studies suggest an abnormality in dyslexia affecting some part of the visual system that is fast and transient and has high contrast sensitivity and low spatial selectivity. Exactly, these properties characterize the magnocellular pathway of the visual system. Accordingly, Applicants in a physiological study measured the visual temporal resolution and contrast sensitivity of normal and dyslexic subjects, and correlated these physiological results with anatomical observations in autopsy specimens. As a result, Applicants have discovered a correlation between defects in the magnocellular pathway and dyslexia. Specifically, Applicants found that dyslexic subjects showed diminished visually evoked potentials to rapid low contrast stimuli but normal responses to slow, high-contrast stimuli. Such abnormalities in the dyslexic subject's evoked potentials were consistent with defective (reduced size) cells found in the magnocellular pathway. Further details and discussion of this study are presented in "Physiological and Anatomical Evidence For a Magnocellular Defect in Developmental Dyslexia" by Margaret S. Livingstone et al., *Proc. of the National Academy of Sciences USA*, Vol. 88, page 7943–7947, Sep. '91, herein incorporated by reference.

As such, the present invention provides apparatus and method of determining defective magnocellular pathway or subdivision of the visual system. In particular, the present invention provides apparatus and method for determining dyslexia.

In general, the present invention presents to a subject eye a series of patterns of spatially varying light intensity. Each pattern provides a degree of contrast between areas of varying light intensity, and different patterns have different degrees of contrast between respective areas of varying light intensity. For each pattern as presented, the present invention measures response of the eye and compares the measured response to a predetermined range of standard/normal responses. That is, the standard responses are indicative of a non-defective magnocellular pathway, and measured responses which fall outside of the predetermined range indicate a magnocellular pathway defect. Likewise, measured responses which fall outside of the predetermined range are deterministic of dyslexia.

In a preferred embodiment, the series of patterns that are presented to the subject eye are checkerboard patterns. Within the series, each checkerboard pattern provides a certain respective degree of contrast between areas of spatially varying light intensity. To that end, different checkerboard patterns provide different respective degrees of contrast. Also for each checkerboard pattern of the series, the checkerboard pattern is alternately displayed with a corresponding contrast reversed pattern. That is, the light and dark areas of the checkerboard pattern are swapped to form the corresponding contrast reverse pattern. The degree of contrast between the light and dark areas however is the same in the checkerboard pattern and its corresponding contrast reverse pattern. Preferably, the alternating display between a checkerboard pattern and its contrast reverse pattern is at a frequency between about 0.5 Hz and 15 Hz.

The preferred embodiment measures response of the eye to the patterns by obtaining a visually evoked potential of the eye for each pattern. Multiple visually evoked potentials per pattern are averaged to provide a working measured response of the eye to the respective pattern. The working measured response is then digitized for comparing to standard responses.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1A:
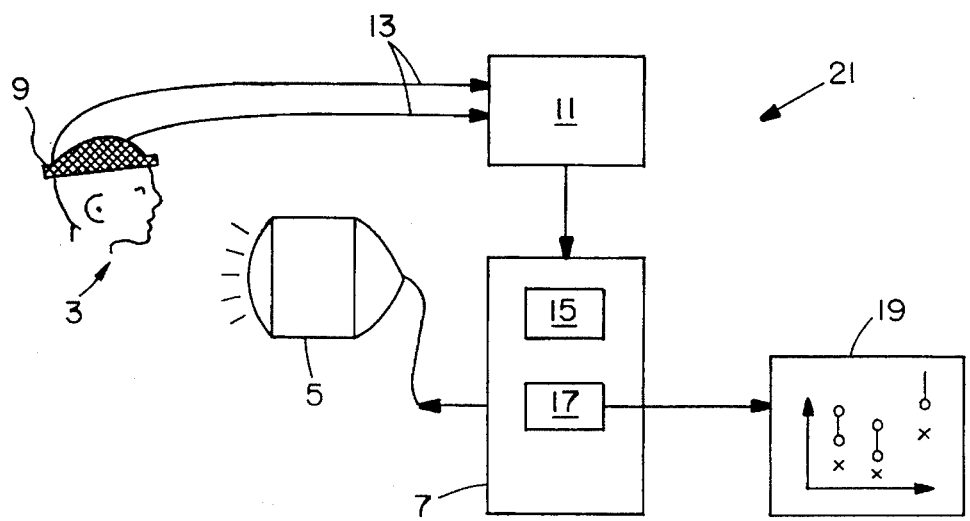
FIG. 1a is a block diagram of apparatus embodying the present invention.

Illustrated in FIG. 1a is apparatus embodying the present invention for detecting magnocellular pathway defects and hence, dyslexia in a subject 3. The apparatus 21 includes a computer 7, display unit 5 coupled to receive output from the computer, electrode assembly 9 coupled to subject 3, and a signal averager 11 connected in series between electrode assembly 9 and computer 7 for providing input to the computer. Preferably, computer 7 is of the minicomputer, PC or similar type digital processor. Display unit 5 is a monochrome, raster scan monitor or of similar CRT (cathode-ray tube) type. Electrode assembly 9 is the type common in the art for measuring visually evoked potentials. And signal averager 11 is for example, a Grass Bio-response averager, model BA10CD or the like.

In more particular terms, computer 7 generates a series of patterns spatially varying in light intensities and displays the patterns before the subject 3 on the screen of display unit 5. The displayed series of patterns serve as visual stimuli to subject 3. In the preferred embodiment, a series of checkerboard patterns is employed. As used herein a "checkerboard pattern" is a pattern having rows and columns formed of a series of adjacent rectangular areas. Every other rectangular area along the rows and columns are of one light intensity while every odd rectangular area along the rows and columns are of another (especially a contrasting) light intensity. In particular, each pixel of a rectangular area is mathematically defined and such definition is repeated for like rectangular areas.

Each checkerboard pattern provides a degree of contrast between areas of spatially varying light intensity. The degree of contrast is preferably in the range of about 2% (very low contrast) to about 50% (high contrast). This degree of contrast differs from checkerboard pattern to checkerboard pattern within the series. Also for each checkerboard pattern, computer 7 displays the pattern for a length of time and then displays the contrast reversal of that pattern. Various contrast reversal rates and temporal frequency throughout the series of patterns are used. Further details of the series of patterns employed by the present invention are discussed below.

The subject eye responds to each pattern displayed on display unit 5 in the form of generating a voltage potential across the visual cortex. This is known as the visually evoked potential. The visual system does not respond instantaneously but responds to the displayed pattern with a characteristic length of time of about 0.1 second or greater. When the visual cortex responds, the electrode assembly 9 which has an occipital electrode connected to the visual cortex of subject 3 generates a voltage signal. The voltage signal is a measurement of the visually evoked potential and is indicative of the response of the brain to the pattern that has been displayed prior to that time. The voltage signals (or measurements of visually evoked potentials) are transmitted from the electrode assembly 9 through lines 13 to signal averager 11.

Signal averager 11 is synchronized or phase locked to the presentation of the patterns on display unit 5. For each pattern signal averager 11 stores and adds the voltage signals received from the eye's response to the pattern. The sum of received voltage signals is divided by the number of voltage signals stored and added for a displayed pattern, to provide an average voltage signal of the eye to the particular pattern. The average of voltage signals serves to (a) improve the signal-to-noise ratio in the electrode assembly 9 detection scheme, and (b) time lock the detected responses to each visual stimulus (displayed pattern).

For a given displayed pattern, signal averager 11 passes the average voltage signal to computer 7. In turn, computer 7 relates the response of the eye as indicated by the average voltage signal to the generated and displayed pattern which caused the response. This is accomplished as follows. At 15 in FIG. 1a, computer 7 digitizes the received average voltage signal by employing an analog-to-digital converter device or similar digitizing board/card as common in the art. Computer 7 then passes the digitized signal (indicative of averaged voltage response of the eye to a displayed pattern) to a Fourier transform routine 17. The purpose of the Fourier transform routine 17 is to quantify and separate energy from noise in the digitized signal/averaged voltage response. As such, for each displayed pattern, the Fourier transform routine 17 provides a measurement of power of the averaged voltage response to that pattern.

Details of the Fourier transform routine 17 used in the preferred embodiment are found in "Numerical Recipes in C" by William H. Press et al., Chapter 12, pages 407–408 and 411–412 (1988). In particular, software code (written in C) for a fast Fourier transform which computes the discrete Fourier transform of N points is given on pages 411–412 of that reference and is herein incorporated by reference (copy attached).

The Fourier transform measurements of responses by subject 3 to the series of displayed patterns are plotted against a predetermined range of standard (normal) responses to the patterns. The predetermined range of standard responses is established from the Fourier transform measurements of a group of control subjects (i.e., subjects without magnocellular pathway defects and hence nondyslexic). As a result of the foregoing plotting, a comparative graph 19 is provided on output of computer 7.

Figure 1B:
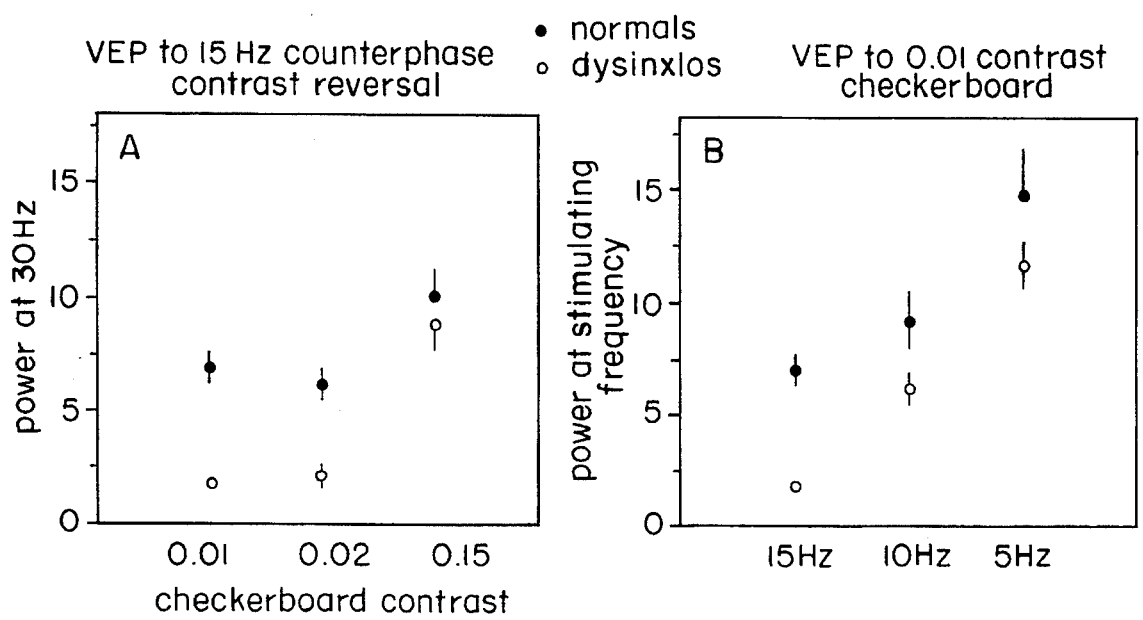
FIG. 1b is an illustration of a graphical output of the apparatus of FIG. 1a showing evoked potentials of a subject in comparison to the predetermined range of normal responses.

In a preferred embodiment, the Fourier transform measurements of responses by subject 3 with respect to that of control subjects are provided in a Fourier spectrum analysis of evoked potentials at different degrees of contrast and different stimulation frequencies of the displayed patterns. FIG. 1b is illustrative of such a Fourier spectrum analysis. The ordinate (y-axis) indicates the power of the Fourier spectrum at the same frequency as the contrast reversal rate (two times the stimulus cycle rate) of the visual stimulus (displayed pattern). The orthogonal axis (x-axis) indicates the contrast level within the displayed pattern where contrast is expressed as a Michelson fraction $(L_{max}-L_{min})/(L_{max}+L_{min})$. Luminance L is the light intensities found in the stimulus (pattern). The darkened circles and associated lines indicate the range of normal responses while the unfilled circles indicate responses by the subject 3.

By way of illustration and not limitation, example ranges of normal responses of various contrast levels of checkerboard patterns and stimulation frequencies are outlined in Table I below.

TABLE I

| Normal Responses (Fourier Power) | Checkerboard Contrast (Michelson Fraction) | Stimulus Frequency (Hz) | Contrast Reversal Rate (Hz) |
|---|---|---|---|
| 14–17 | .01 | 2.5 | .5 |
| 8–11 |  | 5 | 5 |
| 6–8 |  | 7.5 | 10 |
|  | .02 | 2.5 | .5 |
|  |  | 5 | 5 |
| 6–7 |  | 7.5 | 10 |
|  | .15 | 2.5 | .5 |
|  |  | 5 | 5 |
| 10–12 |  | 7.5 | 10 |

It is understood that other contrast patterns besides or in addition to checkerboard patterns may be used as stimuli. In cases of other contrast patterns used as stimuli, the ranges of normal responses may be different than those shown in Table I above.

Figure 2A:
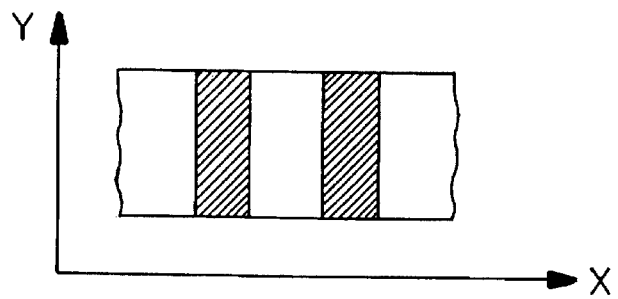
FIGS. 2a–2c are schematics of spatially varying patterns along an x axis, y axis and both axes respectfully.
Figure 2B:
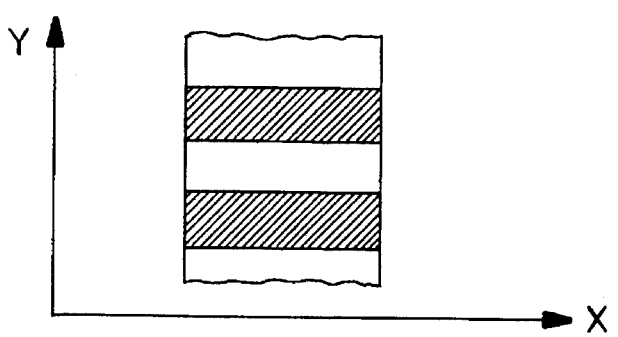
Figure 2C:
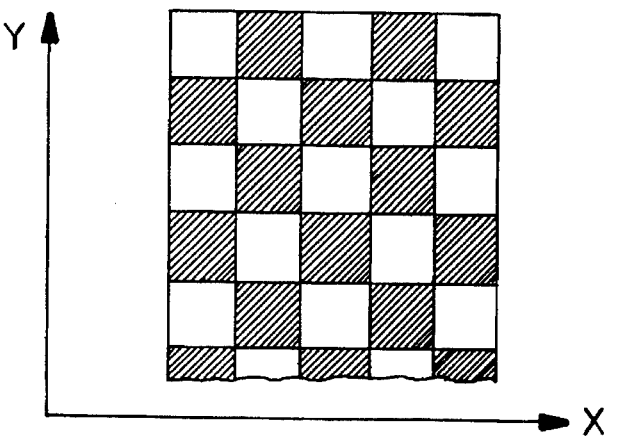

Turning to the specifics of the series of display patterns (stimuli) and in particular the preferred checkerboard pattern employed by apparatus 21 of FIG. 1a, FIGS. 2a–2c and 3a3c are illustrative. FIG. 2a shows a pattern spatially varying in light intensity along the x-axis. The pattern changes from a light column or area to a dark column or area and back to a light column or area from left to right. In a like manner, FIG. 2b illustrates spatial variance in light intensity along the y-axis. This time the pattern changes from a light row to a dark row to a light row from bottom to top. FIG. 2c illustrates a pattern spatially varying in light intensity along both the x and y-axes. Hence, the changing from light to dark to light areas occurs both from left to right and from top to bottom.

Also, the changes from light to dark areas in the patterns of FIGS. 2a–2c are abrupt. This may be described as a square wave, spatial variance in light intensity.

To generate the pattern spatially varying in light intensity along both x and y-axes, and hence the checkerboard pattern of FIG. 2c, computer 7 of FIG. 1a executes a graphics routine as follows. The graphics routine first determines the dimensions (i.e., width and height) of each square or rectangular area of the checkerboard pattern. This is accomplished be determining the number of pixels wide and the number of pixels high the screen of display unit 5 is. The graphics routine then divides the determined screen width by the desired number of squares per row and divides the determined screen height by the number of rows desired in the checkerboard pattern. The graphics routine next paints the screen a first color or brightness (referred to as the background color). Then according to calculated dimensions of each checkerboard square, the routine fills every other square of that size with a contrasting color (referred to as foreground color) along a row. The routine repeats the square filling step along other rows in a staggered manner to produce the checkerboard pattern.

Pseudo code illustrating the above graphics routine producing a checkerboard pattern of 10 rows with 15 squares per row follows.

| *CHECKERBOARD GRAPHICS ROUTINE* | |
|---|---|
| SqWdth = (screenright − screenleft)/15 | *get width of single checkerboard square* |
| Sqht = (screenbtm − screentop)/10 | *get height of single checkerboard square* |
| x=y=o | *start in screen upper corner* |
| color = bkgnd color=1 | *begin with 1st color* |
| Fcolor = 0 | *set foreground color* |
| for j = 0 to 9 do | *for each of 10 rows* |
|   for i = 0 to 14 do | *for each of 15 columns in a given row* |
|     color = [(i+j)mod 2]+Fcolor | *for every other column set color to foreground color and for every odd column set color to background color* |
|     setfillstyle (SOLID_FILL, color) | *set color of given square* |
|     bar(x,y,x+sqWdth,y+sqht) | *draw the square* |
|     x=x+SqWdth+1 | *advance to next column* |
|   end (*of column loop*); | |
|   x=0 | *go to 1st column* |
|   y=y+Sqht+1 | *go to next row* |
| end (*of row loop*) | |
| flicker(); | *present for desired time and contrast reverse* |
| end. | |

Alternative to the above described graphics routine, the series of checkerboard patterns may be generated by a Grass visual pattern generator or similar software executable by computer 7. And the contrast reversal of checkerboard patterns may be generated by similar software. For example, an alternative graphics routine provides columns of equal width, alternating between a certain fixed light and dark intensity, in the pattern of FIG. 2a. The alternative graphics routine overlays or superimposes on that pattern, the pattern of FIG. 2b with each row having a height equal to the column width of the pattern of FIG. 2a, and with rows alternating between the same fixed light and dark intensities as the pattern of FIG. 2a. For each of the light rows of the pattern of FIG. 2b, the alternative graphics routine AND's together the light intensity of that row with the light intensities of the row area of the pattern of FIG. 2a on which it is superimposed. As such, corresponding areas (the area of the pattern of FIG. 2a under the area of the pattern of FIG. 2b) in which both patterns are light result in a light rectangular area. And corresponding areas in which the patterns are different (i.e., one light and one dark) are made to result in a dark rectangular area. The resulting rectangular areas form the pattern of every other row of the desired checkerboard pattern of FIG. 2c.

To form every odd row of the desired checkerboard pattern, the alternative graphics routine similarly processes each of the dark rows of the pattern of FIG. 2b. Specifically for each of the dark rows of the pattern of FIG. 2b, the graphics routine NAND's together the light intensity of that row with the light intensities of the row area of the pattern of FIG. 2a on which it is superimposed. As such, corresponding areas (the area of FIG. 2a under the area of FIG. 2b) in which both patterns are dark result in a light rectangular area. And corresponding areas in which the patterns are different (one light and one dark) are made to result in a dark rectangular area.

Figure 3A:
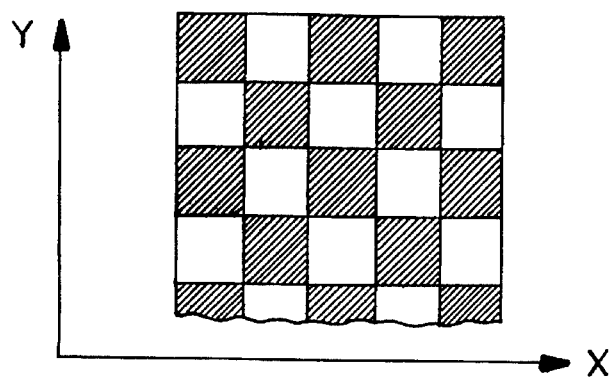
FIGS. 3a–3c are schematics of a contrast reversal of the pattern of FIG. 2c and the pattern of FIG. 2c in different contrast levels.

In effect, the foregoing alternative graphics routine provides the light rows of the FIG. 2b pattern to be transparent such that the light intensity of the FIG. 2a pattern underlying those rows shows through, i.e., remains the same light intensities in the resulting checkerboard pattern. And the dark rows of the FIG. 2b pattern effectively invert (reverse) the light intensities of the FIG. 2a pattern underlying those rows to provide every odd row in the resulting checkerboard pattern. To that end, to generate a contrast reversal pattern of a produced checkerboard pattern, the light rows of the FIG. 2b pattern are used as the inverting (reversing) rows and the dark rows of the FIG. 2b pattern are used as the transparent rows in combining (NANDing and ANDing respectively) the patterns of FIGS. 2a and 2b. The resulting contrast reversal pattern of FIG. 2c is illustrated in FIG. 3a, generated by swapping the inverting and transparent functionality of the rows of the FIG. 2b pattern.

As noted above, the preferred checkerboard pattern has an abrupt spatial variance in light intensity. That is, changes between light and dark intensities in a checkerboard pattern are made without intermediate areas of gray intensities. As such, each checkerboard pattern provides a certain respective degree or level of contrast between the light and dark rectangular areas forming the checkerboard pattern.

In the preferred embodiment, the level or degree of contrast changes between each checkerboard pattern in the series of patterns displayed in the apparatus 21 of FIG. 1a. In the above described alternative graphics routine this changing of contrast level from one checkerboard pattern to the next is accomplished by changing the fixed value of light and dark intensities in the FIGS. 2a and 2b patterns used by the alternative graphics routine in generating the checkerboard patterns. For example, on a gray scale of zero (whitest) through 127 (darkest) light intensities, one checkerboard pattern in the series of displayed patterns comprises every other rectangular area of whitest (zero) light intensity and every odd rectangular area of darkest (127) light intensity. A second or succeeding checkerboard pattern in the series has every other rectangular area of medium white (e.g., grayscale 25) and every odd rectangular area of medium dark/gray (e.g., grayscale 100). A following or third checkerboard pattern in the series has every other rectangular area of light gray (e.g., grayscale 60) and every odd rectangular area of medium gray (e.g., grayscale 90); and so on.

Figure 3B:
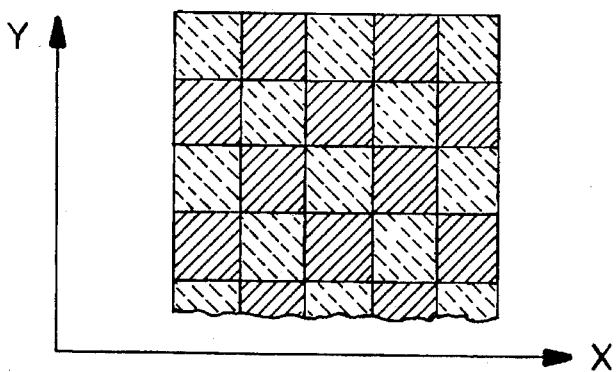
Figure 3C:
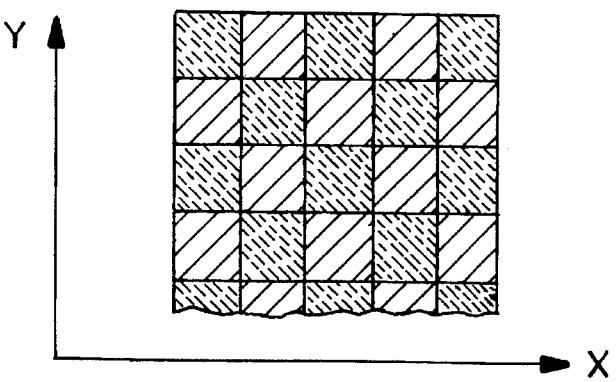

In the foregoing example, the degree or level of contrast changes from a highest degree of contrast in the first pattern to a barely contrasting checkerboard pattern in the third pattern, the second pattern being of an intermediate level of contrast. The patterns of FIGS. 2c and 3b–3c are illustrative, where the checkerboard pattern of FIG. 2c is representative of a highest degree of contrast, the checkerboard pattern of FIG. 3b is representative of an intermediate degree of contrast, and the checkerboard pattern as FIG. 3c is representative of a low degree of contrast. It is understood, that other checkerboard patterns of intermediate levels of contrast are similarly used in the series of patterns displayed to subject 3.

In practice, each checkerboard pattern is about 24×18.5 centimeters and consists of 36 rectangles, each 4×3 centimeters, presented at a viewing distance of 60 centimeters. Spatial frequency is thus about 0.16 cycle per degree vertically and 0.12 cycle per degree horizontally. For each checkerboard pattern in the series of patterns displayed by apparatus 21 of FIG. 1, the checkerboard pattern is displayed for about 1 second and is then reversed in a counterphase square wave temporal pattern at 0.5 Hz (1 contrast reversal per second). Other frequencies for contrast reversing each of the checkerboard patterns are also suitable, for example in the range of about 0.5 Hz through 15 Hz. After alternating between a checkerboard pattern and its corresponding contrast reversal for a total of about 2 seconds, the next checkerboard pattern in the series is displayed in a similar fashion. That succeeding checkerboard pattern is of a different level or degree of contrast than the first displayed checkerboard pattern. Preferably, a series of checkerboard patterns is presented 32 times, each pattern within the series and it's contrast reversal being displayed for about 1 second or less each. Thus, the rate at which the checkerboard patterns having different respective degrees of contrast in the series are displayed is preferably between about 30 patterns per minute and hundreds of patterns per minute.

Equivalents

While the invention has been particularly shown and described with reference to a preferred embodiment thereof, it will be understood by those skilled in the art that various changes in form and details may be made therein without departing from the spirit and scope of the invention as defined by the appended claims.

For example, the electrode assembly 9 of FIG. 1a may include an electrode placed on the eye that produces the electroretinogram (ERG) response of the eye to each displayed pattern. Alternatively, a magnetoretinogram (MRG) or other response may be used. Further, the electrode assembly 9 may comprise a head band coupled to the necessary electrodes and conveniently worn about the head of the subject 3. It is understood by those skilled in the art that other configurations for coupling the electrodes to the subject 3 are suitable.

Also a preamplifier may be used in combination with the signal averager 11 (FIG. 1a) as needed. Further, any such preamplification and signal averaging (including synchronization or phase locking to the timing of the stimuli) may be accomplished within computer 7 by hardware, software or a combination thereof. Other combinations or configurations of the functions served by a preamplifier, the signal averager and computer 7 as described above in FIG. 1a are understood by those skilled in the art to be within the scope of the present invention.

We claim:

1. A method of determining defective magnocellular pathway in a visual system of an eye, comprising the steps of:

providing a series of patterns of spatially varying light intensity, each pattern providing a degree of contrast between areas of varying light intensity and different patterns having different degrees of contrast between respective areas of varying light intensity, the degrees of contrast being in the range of about 1% to 50%;

providing a subject eye having a visual system comprising a magnocellular pathway and a parvocellular pathway;

obtaining from the subject eye a magnocellular pathway signal alone, said signal being indicative of the processing by the magnocellular pathway of the eye independent of processing by the parvocellular pathway of the eye, said obtaining the magnocellular pathway signal alone by (i) presenting to the subject eye the series of patterns at a sufficient stimulation frequency such that the patterns serve as rapid low contrast stimuli to the eye for processing by the magnocellular pathway of the eye, and (ii) for each pattern, measuring a steady state response of the eye specific to the magnocellular pathway response of the eye; and using computer means, (a) receiving the measured responses and (b) plotting the measured responses against a predetermined range of standard responses to the patterns, the predetermined range of standard responses being from target visual systems having non-defective magnocellular pathways, said plotting providing measured responses outside of the predetermined range when there is a defect in the magnocellular pathway and said plotting enabling a comparative graph to be generated as output from the computer means, the comparative graph providing an indication of the defect in the magnocellular pathway.

2. A method as claimed in claim 1 wherein the step of presenting a series of patterns includes presenting a series of checkerboard patterns, each checkerboard pattern having a certain degree of contrast between areas of spatially varying light intensity such that each checkerboard pattern provides a different degree of contrast than the other checkerboard patterns in the series 3. A method as claimed in claim 2 wherein the step of presenting a series of patterns further includes for each checkerboard pattern, alternating display of the pattern with its contrast reversed pattern.

4. A method as claimed in claim 3 wherein the step of alternating display of a checkerboard pattern is at a frequency between about 0.5 Hz and about 15 Hz.

5. A method as claimed in claim 1 wherein the step of presenting a series of patterns includes presenting a series of temporally varying patterns.

6. A method as claimed in claim 1 wherein the step of measuring response of the eye includes obtaining a visually evoked potential of the eye.

7. A method as claimed in claim 1 wherein the step of measuring response of the eye includes for each pattern, averaging multiple responses of the eye to provide the measured response of the eye to the pattern.

8. A method as claimed in claim 1 wherein the step of plotting the measured responses includes digitizing the measured responses.

9. A method as claimed in claim 1 further comprising the step of determining dyslexia, where the measured response is outside the predetermined range.

10. For a subject eye having a magnocellular pathway and a parvocellular pathway, apparatus for determining magnocellular pathway defects in the subject eye comprising:

a series of patterns spatially varying in light intensity, each pattern providing a degree of contrast between areas of varying light intensity, and different patterns having different degrees of contrast between respective areas of varying light intensity, the degrees of contrast being between about 1% to about 50%;

a response assembly for obtaining from the subject eye a magnocellular pathway response alone, the magnocellular pathway response being indicative of processing by the magnocellular pathway independent of processing by the parvocellular pathway, the response assembly including (i) display means for presenting to the subject eye the series of patterns at a sufficient stimulation frequency between about 0.5 Hz and 15 Hz such that the patterns serve as rapid low contrast stimuli to the eye for processing by the magnocellular pathway of the subject eye, and (ii) means for measuring, for each pattern, steady state response of the eye specific to the magnocellular pathway response of the eye, said measuring means providing magnocellular pathway signals indicative of processing by the magnocellular pathway of the eye independent of processing by the parvocellular pathway; and computer means coupled to the measuring means of the response assembly for receiving the magnocellular pathway signals from the measuring means, said computer means being responsive to the magnocellular pathway signals in a manner which relates the signal indicated responses to the corresponding patterns and plots the signal indicated responses against a predefined range of standard responses for the corresponding patterns, the predefined range of standard responses being from target subjects having non-defective magnocellular pathways, such that the computer means plots signal indicated responses outside of the predetermined range when there is a magnocellular pathway defect in the visual system of the subject eye, said plotting enabling a comparative graph of the signal indicated responses with respect to the predetermined range of standard responses to be output from the computer means.

11. Apparatus as claimed in claim 10 wherein the series of patterns includes a series of checkerboard patterns, each checkerboard pattern having a certain degree of contrast between areas of spatially varying light intensities such that each checkerboard pattern provides a different degree of contrast than the other checkerboard patterns in the series.

12. Apparatus as claimed in claim 11 wherein for each checkerboard pattern, the display means alternately displays the pattern with a corresponding contrast reverse pattern.

13. Apparatus as claimed in claim 12 wherein the display means alternates display between a checkerboard pattern and its contrast reverse pattern at a frequency between about 0.5 Hz and about 15 Hz.

14. Apparatus as claimed in claim 10 wherein the series of patterns further vary temporally.

15. Apparatus as claimed in claim 14 wherein the temporal frequency is greater than about 30 patterns per minute.

16. Apparatus as claimed in claim 10 wherein the means for measuring includes means for obtaining a visually evoked potential of the eye.

17. Apparatus as claimed in claim 10 further comprising a signal averager receiving signals from the measuring means and providing to the computer means an average of the signals for each pattern.

18. Apparatus as claimed in claim 10 wherein the computer means include a digitizer for digitizing the signals received from the measuring means.

19. A method of detecting dyslexia comprising the steps of:

providing a series of temporally varying patterns of spatially varying light intensity, each pattern providing a certain degree of contrast between areas of varying light intensity and different patterns having different degrees of contrast between respective areas of varying light intensity, the degrees of contrast being in the range of about 1% to about 50%;

providing a subject eye having a visual system comprising a magnocellular pathway and a parvocellular pathway;

obtaining from the subject eye a magnocellular pathway signal alone, said signal being indicative of processing by the magnocellular pathway independent of processing by the parvocellular pathway, said obtaining the magnocellular pathway signal alone by (i) presenting to the subject eye the series of patterns at a sufficient stimulation frequency such that the patterns serve as rapid low contrast stimuli to the eye, and (ii) for each pattern, measuring response of the eye specific to the magnocellular pathway response of the eye, including obtaining a steady state visually evoked potential of the eye; and using computer means receiving the measured responses and plotting the measured responses against a predetermined range of normal responses to the series of patterns, the predetermined range of normal responses being from non-dyslexic target visual systems, said plotting providing measured responses outside of the predetermined range when there is a case of dyslexia, and said plotting enabling a comparative graph of the measured responses with respect to the predetermined range of normal responses to be output by the computer means for indicating a case of dyslexia.

20. A method as claimed in claim 19 wherein the step of providing a series of patterns includes providing a series of checkerboard patterns, each checkerboard pattern having a certain degree of contrast between areas of spatially varying light intensity such that each checkerboard pattern provides a different degree of contrast than the other checkerboard patterns in the series.

21. A method as claimed in claim 20 wherein the step of providing a series of checkerboard patterns further includes for each checkerboard pattern, alternating display of the pattern with its contrast reversed pattern.

22. A method as claimed in claim 21 wherein the step of alternating display of a checkerboard pattern with its contrast reverse pattern is at a frequency between about 0.5 Hz and about 15 Hz.

23. Apparatus for determining dyslexia in a subject eye having a magnocellular pathway and a parvocellular pathway, the apparatus comprising:

a series of temporally varying patterns of spatially varying light intensity, each pattern providing a certain degree of contrast between areas of varying light intensity, and different patterns having different degree of contrast between respective areas of varying light intensity, the degrees of contrast being between about 1% to about 50%;

a response assembly for obtaining a magnocellular pathway response alone of the subject eye indicative of processing by the magnocellular pathway independent of the parvocellular pathway, the response assembly including (i) display means for presenting to the subject eye the series of patterns at a sufficient stimulation frequency between about 0.5 Hz and 15 Hz such that the patterns serve as rapid, low contrast stimuli to the eye, and (ii) for each pattern, means for measuring response of the eye specific to the magnocellular pathway response of the eye, including at least a steady state visually evoked potential of the eye, the means for measuring providing magnocellular pathway signals alone, said signals being indicative of the magnocellular pathway response of the eye independent of parvocellular pathway response of the eye; and computer means coupled to the measuring means and responsive to the magnocellular pathway signals from the measuring means in a manner which relates the signal indicated responses to the corresponding patterns and plots the signal indicated responses against a predefined range of normal responses for the corresponding patterns, the predefined range of normal responses being from non-dyslexic target subjects having non-defective magnocellular pathways, such that the computer means plots signal indicated responses outside of the predefined range in the case of dyslexia, and on output the computer means generates a comparative graph of the signal indicated responses with respect to the predefined range of normal responses, said graph indicating a case of dyslexia.

24. Apparatus as claimed in claim 23 wherein the series of patterns includes a series of checkerboard patterns, each checkerboard pattern having a certain degree of contrast between areas of spatially varying light intensity, each checkerboard pattern providing a different degree of contrast than the other checkerboard patterns in the series.

25. Apparatus as claimed in claim 24 wherein for each checkerboard pattern, the display means alternates display of that pattern with a corresponding contrast reversed pattern.

26. Apparatus as claimed in claim 25 wherein the display means alternates display between a checkerboard pattern and its contrast reverse pattern at a frequency between about 0.5 Hz and about 15 Hz.

\* \* \* \* \*